United States Patent

Stein

[11] 4,289,885
[45] Sep. 15, 1981

[54] 3-[2-(DIMETHYLAMINO)-2-PHENYLETHYL]N-[PHENYLAMINO)CARBONYL]-SYDNONE IMINE, A NEW CENTRAL NERVOUS SYSTEM STIMULANT

[75] Inventor: Reinhardt P. Stein, Audubon, Pa.

[73] Assignee: American Home Products Corporation, New York, N.Y.

[21] Appl. No.: 193,043

[22] Filed: Oct. 2, 1980

[51] Int. Cl.³ .................. C07D 271/04; C07D 413/06
[52] U.S. Cl. .................................. 548/125; 544/138; 544/367; 546/209
[58] Field of Search ................ 544/138, 367; 546/209; 548/125

[56] References Cited

U.S. PATENT DOCUMENTS 3,277,108 10/1966 Daeniker ............................. 548/125

FOREIGN PATENT DOCUMENTS 2028880 12/1971 Fed. Rep. of Germany.
2738022 6/1978 Fed. Rep. of Germany.
329890 11/1972 U.S.S.R.
222370 5/1973 U.S.S.R.

OTHER PUBLICATIONS

Olovyanishinkiva et al., Khim. Geterotsikl Soedin, vol. 2 (1978), pp. 170–175, and vol. 9 (1975), pp. 1198–1203.
Yashunskii et al.; J. Med. Chem., 00/14 (1971), pp. 1013–1015.
Polgar et al., Xenobiotica, vol. 9, (1979), pp. 511–520.
Polgar et al., Acta Pharm. Hung., vol. 48, pp. 23–24, (1978).
Kholodov et al., Mater. Resp. Rasshir. Konf., Farmacol. Gruz, 2nd (1977), pp. 84–85.

Primary Examiner—Henry R. Jiles
Assistant Examiner—R. W. Ramsuer
Attorney, Agent, or Firm—Richard K. Jackson

[57] ABSTRACT

A compound of the formula:

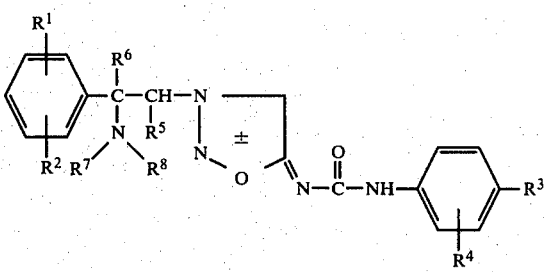

in which
$R^1$ and $R^2$ are, independently, hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms or alkoxycarbonyl of 2 to 4 carbon atoms;

$R^3$ is hydrogen, halo, nitro or alkanoyl of 2 to 4 carbon atoms;

$R^4$ is hydrogen, halo, nitro or perfluoroalkyl of 1 to 3 carbon atoms;

$R^5$ and $R^6$ are, independently, hydrogen or methyl; and $R^7$ and $R^8$ are, independently, alkyl of 1 to 4 carbon atoms, or when taken with the nitrogen atom to which they are attached form a piperidinyl, pyrolidinyl, morpholinyl, N-alkyl piperazinyl in which the alkyl group contains from 1 to 6 carbon atoms or N-phenylpiperazinyl group or a non-toxic acid addition salt thereof, are central nervous system stimulants.

8 Claims, No Drawings

3-[2-(DIMETHYLAMINO)-2-PHENYLETHYL]N-[PHENYLAMINO)CARBONYL]SYDNONE IMINE, A NEW CENTRAL NERVOUS SYSTEM STIMULANT

BACKGROUND OF THE INVENTION

After the discovery of the central nervous system stimulatory properties of 3-(1-methyl-2-phenylethyl)-N-(phenylcarbamoyl)sydnone imine (Sydnocarb; U.S.S.R. 329,890 and Offenlegungsschrift No. 2,028,880) various analogues have been reported. U.S.S.R. 222,370 and Offenlegungsschrift No. 2,738,022 disclose sydnone imines which contain phenyl, 1- or 2-phenylethyl and the phenylisopropyl groups in 3-position as well as N-meta- and para-chlorophenyl and N-phenyl carbamoyl groups. Variations of 3-benzyl sydnonimines are disclosed in U.S. Pat. No. 3,277,108. Other variously substituted 3-aralkyl sydnonimines are disclosed by Olovyanishinkiva et al., Khim. Geterotsikl Soedin, 2 170-175 (1978) and 9 1198-1203 (1975).

Sydnocarb is conventionally produced by cyanomethylation of amphetamine followed by nitrosation and ring closure with a mineral acid yielding sydnophen as an acid halide salt which is reacted with phenylisocyanate under mildly basic conditions to introduce the N-phenylcarbamoyl group. As an asymmetric compound, amphetamine may be employed as the initial reactant as the racemic d,l-mixture or as the pure d- or l-isomer to yield racemic or optically active sydnophen and ultimately sydnocarb.

Yashunskii et al., J. Med. Chem., 14 1013–1015 (1971) disclose the marked CNS-stimulatory effect of 3-(1-methyl-2-phenylethyl) sydnonimine (Sydnophen). The relative activities of a large number of alkyl, aryl and aralkylsydnonimines are presented in Table 1 on page 1014. Most of them, including compound XVIII (2-hydroxy-1-methyl-2-phenylethyl-sydnonimine), were essentially inactive central nervous system stimulants relative to compound XIII (Sydnophen), demonstrating the criticality of the structure of the 3-substituent in the Sydnocarb series of compounds as far as CNS stimulatory activity is concerned. Thus, although the activity profile of Sydnocarb is not identical to that of amphetamine, or for that matter Sydnophen, CNS stimulatory activity is a common property of the initial reactant amphetamine, the intermediate Sydnophen and the final product Sydnocarb.

Although Sydnocarb and its derivatives disclosed in the literature forms salts with various organic and inorganic acids, such salts are not appreciably water soluble and when stirred in water, the complex or adduct salt is broken up to reisolate the neutral mesoionic sydnone imine substrate.

The metabolites of Sydnocarb have been studied by several groups. L. E. Kholodov and E. T. lilin, Mater. Resp. Rasshir. Konf. Farmacol. Gruz. 2nd 1977, 84-5 report finding hydroxylation of Sydnocarb at the beta carbon of the phenylisopropyl substituent and at the phenyl ring of the phenylcarbamoyl group, hydrolytic cleavage of the phenylcarbamoyl group and ring opening of the heterocyclic nucleus. They report that the psychostimulating activity of Sydnocarb is a property of that compound and not its metabolites. Polgar et al. Acta. Pharma. Hung., 48, Suppl. 23–24 (1978) and Xenobiotica 9, No. 8, 511–520 (1979) report several hydroxylated metabolites and conjugates of hydroxylated Sydnocarb.

DESCRIPTION OF THE INVENTION

In accordance with this invention there is provided a group of central nervous system stimulants which are 3-(2-amino-2-phenylethyl)-N-[(phenylamino)carbonyl]-sydnonimines optionally substituted in either or both phenyl rings, of the formula:

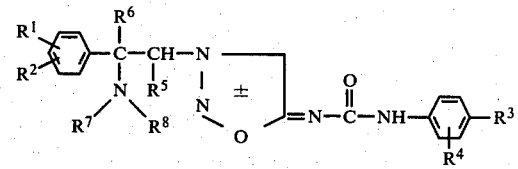

in which
$R^1$ and $R^2$ are, independently, hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms, or alkoxycarbonyl of 2 to 4 carbon atoms;
$R^3$ is hydrogen, halo, nitro or alkanoyl of 2 to 4 carbon atoms;
$R^4$ is hydrogen, halo, nitro or perfluoroalkyl of 1 to 3 carbon atoms;
$R^5$ and $R^6$ are, independently, hydrogen or methyl and
$R^7$ and $R^8$ are, independently, alkyl of 1 to 4 carbon atoms, or when taken with the nitrogen atom to which they are attached, form a piperidinyl, pyrolidinyl, morpholinyl, N-alkyl piperazinyl in which the alkyl group contain from 1 to 6 carbon atoms or N-phenylpiperazinyl group; or
a non-toxic acid addition salt thereof.

It is generally preferred that the halo substituent be chlorine, bromine or fluorine although iodine is acceptable. Likewise, it is preferred that the alkyl and alkoxy substituents be relatively small, the methyl, ethyl, propyl, isopropyl, methoxy, ethoxy, propoxy and isopropoxy groups being preferred. The $R^3$ substituent in 4 position when $R^4$ is hydrogen influences potency to a greater extent than $R^1$, $R^2$ and $R^4$ and is preferably a halogen.

The non-toxic acid addition salts of the compounds of this invention are conventionally produced by the method and from any of the acids disclosed in U.S. Pat. No. 3,277,108. The salts are preferably formed with hydrochloric, hydrobromic, sulfuric, phosphoric, acetic, propionic, oxalic, succinic, maleic, fumeric or hypophosphorous acid. Unlike the sydnone imine salts of the prior art, the salts formed with the aminic bases of this invention are water soluble, dissociating sufficiently to dissolve in aqueous medium to provide a homogeneous solution. Thus, the compounds of this invention may be formulated for administration in aqueous vehicle thereby expanding the routes available for practical dosing to achieve central nervous system stimulation to patients unable to receive treatment orally.

The 3-(2-amino-2-phenylethyl)sydnonimine compounds of this invention contain a chiral center at the benzylic carbon atom and appear as the racemic d,l-mixture which is resolvable into the pure d- and l-isomers. As with Sydnocarb, one of the isomers is expected to possess the major portion of the CNS stimulatory activity and is preferred over the racemic mixture for that reason. Unlike Sydnocarb, the compounds of this invention are derived from a 2-tertiary amino-2-phenylethylamine or 2-tertiary amino-1-methyl-2-phenylethylamine through the intermediate 3-(2-tertiary amino-2-phenylethyl)sydnonomine or 3-((2-tertiary amino-1-methyl-2-phenylethyl)sydnonimine, none of which are known to demonstrate any meaningful central nervous system stimulatory activity. Being derived from reactants and through intermediates which are substantially devoid of activity, the compounds of this invention do not share with Sydnocarb the potential problem of degradative reversion or metabolic conversion back to a precursor which is itself active with a different pharmacological profile. Furthermore, handling of the inactive reactants and/or intermediates involved in this invention poses no problem for the production chemist.

The 3-[(2-tertiary amino-1-methyl-2-phenylethyl)-]sydnonimines and the 3-[(2-tertiary amino-2-methyl-1-methyl-2-phenylethyl)]sydnonimines of this invention contain two chiral centers and provide two racemic mixtures of product. The epimers and optical isomers are readily separable by standard techniques well known to the chemist or by selection of the desired starting material, the product can be limited to a single racemic mixture of isomers.

The activity profile of the compounds of this invention is similar to that of amphetamine in some aspects while being devoid of other activities of amphetamine. For example, like amphetamine the compounds of this invention increase motor activity. However, the compounds of this invention are much less toxic than amphetamine, providing a slower onset of activity (which indicates less euphoria and abuse potential).

The compounds of this invention were shown to possess central nervous system stimulant activity by subjecting them to the following standard test procedure:

Male mice weighing 17 to 25 gms. are injected orally with drug solubilized or suspended in 1% Tween ® 80. Control animals are injected with 1% Tween ® 80.

Six Columbus Instrument Company activity chambers are employed. Three mice given identical treatment are placed in each chamber for all tests. During each run, control animals (1% Tween ® only) occupy 3 chamber; the other 3 chambers measure activity of drug treated animals. For each dose of a given drug the experiment is run two times in a counterbalanced design so that each specific activity chamber records the activity of control animals during one run, and the activity of drug animals on the other run. Thus at each dose level 18 mice are used in the drug group and 18 mice in the control group.

Activity counts are recorded every ten minutes for a period of 2 hours. The data are analyzed using Students "t" test comparing the means of the control and drug groups for each 10 minute period. The drug treated group is compared graphically with the control group in regard to duration of action and dose response at peak drug activity.

As central nervous system stimulants with unique activity profiles, the compounds of this invention are useful in the treatment of anergic disorders (such as sleepiness and fatigue) including related types of depression and narcolepsy. Based upon the potency of the compounds of this invention in use in mice, the dose contemplated for use in the 70 kilogram human would vary from about 35–700 milligrams administered orally once or twice per day under the guidance of a physician. Of course, the dosage regimen as well as the route of administration, oral or parenteral, will vary with the condition of the patient relative to age, severity of depression, etc.

The compounds of this invention are prepared by conventional techniques analogous to those employed in the preparation of Sydnocarb. The starting materials are either known or preparable by routine synthetic methods. Thus, a properly substituted 2-tertiary amino-2-phenylethyl amine is cyanomethylated with a reactant $XCH_2CN$ where X may be —OH, —Br, —Cl, tosyl, and the like to form the intermediate

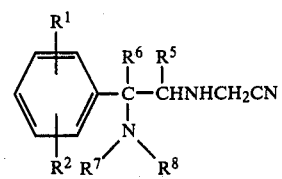

which is nitrosated with an excess of $NaNO_2$ in aqueous HCl to yield

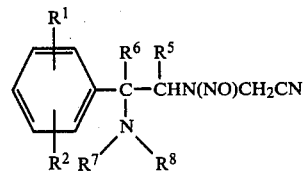

which is then reacted with

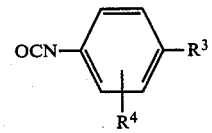

in the presence of an organic amine base, such as triethylamine, 4-dimethylaminopyridine, and the like, following the procedure disclosed in Offenlegungsschrift No. 2,738,022, to yield the desired products.

The following examples illustrate without limitation the process for producing the compounds of this invention. Where the intermediate cyanomethylated product of the phenethyl amine and the N-nitroso derivative thereof are isolated as oils, no attempt was made to obtain the purified intermediate. The activity counts presented at the end of each example represent the difference from control based upon the test procedure disclosed, supra. dl-Sydnocarb demonstrated a difference from control of 939 activity counts at 10 mg/kg., p.o.

EXAMPLE 1 dl-N-Nitroso-N-[2-(dimethylamino)-2-phenylethyl-]amino acetonitrile hydrochloride Dissolve dl-2-dimethylamino-2-phenylethylamine, dihydrochloride (4.74 g.) in water (50 ml.), stir and cool with an ice-bath. Add 37% aqueous formaldehyde solution (2.0 ml.), stir for 10 minutes, then drip in a solution of potassium cyanide (1.30 g.) in water (20 ml.). Stir the cold solution for 1 hour, then cool further to 0° C. (icesalt bath). Drip in a solution of sodium nitrite (1.4 g.) in water (15 ml.) followed by 5 N aqueous HCl (8 ml.). Stir, then again drip in a solution of sodium nitrite (1.4 g.) in water (15 ml.) and continue stirring for 3 hours, allowing the reaction to warm to room temperature. Drip in 5 N aqueous sodium hydroxide solution until a pH of 10 is attained. Quickly extract with diethyl ether, then dry and evaporate the solvent in vacuo. Pump dry, then treat the oil in diethyl ether with decolorizing carbon, filter and evaporate, then pump to obtain the free-base of the title product as an oil (about 3 g.). To characterize this product dissolve a sample (313 mg.) in methylene chloride, treat with 5 N isopropanolic-HCl (1 ml.), then evaporate the solvent in vacuo. Crystallize the residue from acetone, filter to obtain the title product (210 mg.); m.p. 164°–166° C.

Analysis for: $C_{12}H_{16}N_4O\cdot HCl$. Calculated: C, 53.63; H, 6.38; N, 20.85%. Found: C, 53.51; H, 6.34; N, 21.31%.

The crude, oily free-base of the product obtained above is sufficiently pure for subsequent reactions.

EXAMPLE 2 dl-3-[2-(Dimethylamino)-2-phenylethyl]-N-[(phenylamino)carbonyl]sydnone imine, dihydrochloride Stir the oily free base, dl-N-nitroso-N-[2-(dimethylamino)-2-phenylethyl]amino acetonitrile (10.2 g.) with toluene (150 ml.), add phenylisocyanate (5.75 g.) followed by triethylamine (4.44 g.) and heat the mixture at 55° C. for 4 hours. Cool and let stand at room temperature. Evaporate the solvent in vacuo and pump to obtain an oil. Treat the oil in ethyl acetate with decolorizing carbon, filter, then treat the filtrate with 5 N isopropanolic-HCl (20 ml.). Evaporate the solvent in vacuo without the application of heat, triturate the gum with isopropanol containing a little methylene chloride to initiate crystallization. Let stand, then filter to obtain 16.7 g. of the crude title product; m.p. 139°–143° C. (dec). Dissolve the solid in methylene chloride containing a little methanol, treat with decolorizing carbon, filter and evaporate the solvents in vacuo. Cover the oil with acetonitrile, then scratch and triturate to fully crystallize and filter to obtain 8.0 g. of the pure title product as a partial hydrate; m.p. 149°–151° C. (dec).

Analysis for: $C_{19}H_{21}N_5O_2\cdot 2HCl\cdot \tfrac{1}{2}H_2O$. Calculated: C, 53.03; H, 5.54; N, 16.28%. Found: C, 53.17; H, 5.42; N, 16.41%. Activity Counts: 859 at 10 mg/kg.

EXAMPLE 3 dl-3-(2-Dimethylamino-2-phenylethyl)-N-[(4-chlorophenylamino)carbonyl]sydnone imine, dihydrochloride The title compound is prepared following the procedure of Example 2 with the exception that p-chlorophenylisocyanate is employed as the reactant rather than phenylisocyanate, m.p. 150°–153° C.

Analysis for: $C_{19}H_{20}N_5O_2Cl\cdot 2HCl\cdot 1.5H_2O$. Calculated: C, 46.97; H, 5.19; N, 14.42. Found: C, 46.62; H, 4.86; N, 14.18. Activity Counts: 1329 at 10 mg/kg and 431 at 1 mg/kg.

What is claimed is:

1. A compound of the formula:

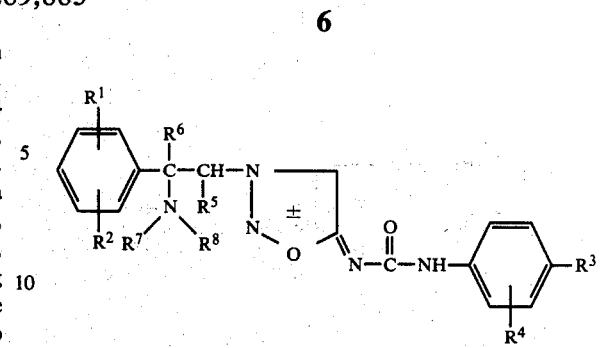

in which $R^1$ and $R^2$ are, independently, hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms or alkoxycarbonyl of 2 to 4 carbon atoms;

$R^3$ is hydrogen, halo, nitro or alkanoyl of 2 to 4 carbon atoms;

$R^4$ is hydrogen, halo, nitro or perfluoroalkyl of 1 to 3 carbon atoms;

$R^5$ and $R^6$ are, independently, hydrogen or methyl; and $R^7$ and $R^8$ are, independently, alkyl of 1 to 4 carbon atoms, or when taken with the nitrogen atom to which they are attached form a piperidinyl, pyrolidinyl, morpholinyl, N-alkyl piperazinyl in which the alkyl group contains from 1 to 6 carbon atoms or N-phenylpiperazinyl group; or a non-toxic acid addition salt thereof.

2. A compound of claim 1 of the formula:

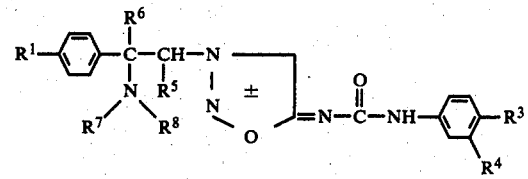

in which $R^1$ is hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms or alkoxycarbonyl of 2 to 4 carbon atoms;

$R^3$ is hydrogen, halo, nitro or alkanoyl of 2 to 4 carbon atoms;

$R^4$ is hydrogen or halo;

$R^5$ and $R^6$ are, independently, hydrogen or methyl; and $R^7$ and $R^8$ are, independently, alkyl of 1 to 4 carbon atoms, or when taken with the nitrogen atom to which they are attached form a piperidinyl, pyrolidinyl, morpholinyl, N-alkyl piperazinyl in which the alkyl group contains from 1 to 6 carbon atoms or N-phenylpiperazinyl group; or a non-toxic acid addition salt thereof.

3. A compound of claim 1 of the formula:

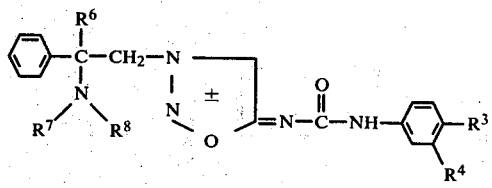

in which

R³ is hydrogen, halo, nitro or alkanoyl of 2 to 4 carbon atoms;

R⁴ is hydrogen or halo;

R⁶ is hydrogen or methyl; and

R⁷ and R⁸ are, independently, alkyl of 1 to 4 carbon atoms, or when taken with the nitrogen atom to which they are attached form a piperidinyl, pyrolidinyl, morpholinyl, N-alkyl piperazinyl in which the alkyl group contains from 1 to 6 carbon atoms or N-phenylpiperazinyl group; or a non-toxic acid addition salt thereof.

4. A compound of claim 1 of the formula:

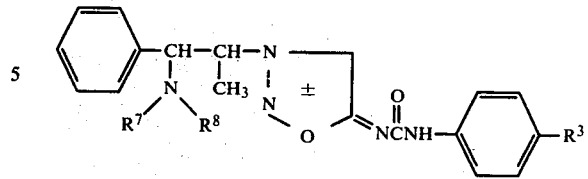

in which

R³ is hydrogen, halo, nitro or alkanoyl of 2 to 4 carbon atoms; and

R⁷ and R⁸ are, independently, alkyl of 1 to 4 carbon atoms, or when taken with the nitrogen atom to which they are attached form a piperidinyl, pyrolidinyl, morpholinyl, N-alkyl piperazinyl in which the alkyl group contains from 1 to 6 carbon atoms or N-phenylpiperazinyl group or a non-toxic acid addition salt thereof.

5. A compound of claim 1 which is dl-3-(2-dimethylamino-2-phenylethyl)-N-[(phenylamino)carbonyl]-sydnone imine or a non-toxic acid addition salt thereof.

6. A compound of claim 1 which is d or l-3-(2-dimethylamino-2-phenylethyl)-N-[(phenylamino)carbonyl]-sydnone imine or a non-toxic acid addition salt thereof.

7. A compound of claim 1 which is dl-3-(2-dimethylamino-2-phenylethyl)-N-[(4-chlorophenylamino)-carbonyl]sydnone imine or a non-toxic acid addition salt thereof.

8. A compound of claim 1 which is d or l-3-(2-dimethylamino-2-phenylethyl)-N-[(4-chlorophenylamino)-carbonyl]sydnone imine or a non-toxic acid addition salt thereof.

* * * * *